(12) United States Patent
Li

(10) Patent No.: US 8,605,281 B2
(45) Date of Patent: Dec. 10, 2013

(54) PROBE HAVING NANO-FINGERS

(75) Inventor: Zhiyong Li, Foster City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 146 days.

(21) Appl. No.: 13/272,987

(22) Filed: Oct. 13, 2011

(65) Prior Publication Data

US 2013/0094020 A1   Apr. 18, 2013

(51) Int. Cl.
*G01J 3/44* (2006.01)

(52) U.S. Cl.
USPC ...................................................... 356/301

(58) Field of Classification Search
USPC ................. 356/301, 72–73; 264/293; 977/953
See application file for complete search history.

(56) References Cited

U.S. PATENT DOCUMENTS

| | | | |
|---|---|---|---|
| 5,677,196 A | 10/1997 | Herron et al. | |
| 6,193,870 B1 | 2/2001 | Morse et al. | |
| 6,222,619 B1 | 4/2001 | Herron et al. | |
| 6,756,795 B2 | 6/2004 | Hunt et al. | |
| 6,777,244 B2 | 8/2004 | Pepper et al. | |
| 7,256,886 B2 | 8/2007 | Cullum et al. | |
| 7,528,948 B2 | 5/2009 | Bratkovski et al. | |
| 7,583,379 B2 | 9/2009 | Zhao et al. | |
| 7,656,525 B2 | 2/2010 | Zhao et al. | |
| 7,667,238 B2 | 2/2010 | Erchak | |
| 7,833,842 B2 | 11/2010 | Williams | |
| 8,108,943 B2 * | 1/2012 | Anderson | 850/30 |
| 2003/0077023 A1 | 4/2003 | Troll | |
| 2006/0038990 A1 | 2/2006 | Habib et al. | |
| 2006/0231381 A1 | 10/2006 | Jensen et al. | |
| 2007/0070341 A1 | 3/2007 | Wang | |
| 2007/0086001 A1 * | 4/2007 | Islam et al. | 356/301 |
| 2008/0017845 A1 | 1/2008 | Drndic et al. | |
| 2008/0024776 A1 | 1/2008 | Bratkovski et al. | |
| 2008/0144026 A1 | 6/2008 | Zhao et al. | |
| 2008/0166706 A1 | 7/2008 | Zhang et al. | |
| 2008/0174775 A1 | 7/2008 | Moskovits et al. | |
| 2008/0187648 A1 | 8/2008 | Hart | |
| 2008/0311028 A1 | 12/2008 | Stanbery | |

(Continued)

FOREIGN PATENT DOCUMENTS

| | | |
|---|---|---|
| EP | 2058908 | 5/2009 |
| JP | 2000-206048 | 7/2000 |

(Continued)

OTHER PUBLICATIONS

Akhavan, O, et al., Physical Bounds of Metallic Nanofingers Obtained by Mechano-chemical Atomic Force Microscope Nanolithography, (Research Paper), Applied Surface Science, Jan. 1, 2009, pp. 3513-3517, vol. 255, No. 6.

(Continued)

*Primary Examiner* — Tarifur Chowdhury
*Assistant Examiner* — Abdullahi Nur

(57) ABSTRACT

A probe for use in a sensing application includes an elongate body having a first end and a free end, wherein the first end is to be attached to a support. The probe also includes a plurality of nano-fingers having respective bases and tips, wherein each of the plurality of nano-fingers is attached to the free end and is composed of a flexible material, and wherein the plurality of nano-fingers are collapsed toward each other such that the tips of the plurality of nano-fingers are substantially in contact with each other.

15 Claims, 4 Drawing Sheets

(56) References Cited

U.S. PATENT DOCUMENTS

| | | |
|---|---|---|
| 2009/0261815 A1 | 10/2009 | Cairns |
| 2009/0303472 A1 | 12/2009 | Zhao et al. |
| 2011/0001118 A1 | 1/2011 | Bhupendra |
| 2011/0030792 A1 | 2/2011 | Miguez |
| 2011/0128537 A1 | 6/2011 | Bond et al. |
| 2012/0107948 A1 | 5/2012 | Li et al. |
| 2012/0212732 A1* | 8/2012 | Santori et al. ............ 356/301 |

FOREIGN PATENT DOCUMENTS

| | | |
|---|---|---|
| WO | WO-2008028521 | 3/2008 |
| WO | WO-2010088585 | 8/2010 |
| WO | WO-2010126640 | 11/2010 |

OTHER PUBLICATIONS

Baldwin, et al. "Integrated Optics Evanescent Wave Surface Enhanced Raman Scattering (IO-EWSERS) of Mercaptopyridines on a Planar Optical Chemical Bench: Binding of Hydrogen and Copper Ion", Langmuir, 1996, vol. 12, pp. 6389-6398.

Cubukcu, E., et al., "Plasmonic Laser Antennas and Related Devices", IEEE Journal of Selected Topics in Quantum Electronics, Nov./Dec. 2008, vol. 14, No. 6, pp. 148-1461.

Fan et al., "Multilayer Silver Nanoparticles Modified Optical Fiber Tip for High Performance SERS Remote Sensing," 217th ECS Meeting—Vancouver, Canada, Apr. 25-Apr. 30, 2010, J2-Electrochemical Nano/Bio Sensors 2, Abs# 1830.

Fan, J. G. et al., "Integrating Aligned Nanorod Array onto Optical Fibers of SERS Probes," Proc. of SPIE—Nanoengineering: Fabrication, Properties, Optics, and Devices III, vol. 6327, 2006, pp. R1 to R10.

Giglymar, Josef, "Nano-Finger Electrodes for th Electro-Optical Generation and Tuning of Gratings at Several Wavelengths", <http://www.ipme.ru/ipme/conf/NN2003/NN2003_Abstracts.pdf> Publication Date: Aug. 30, 2003-Sep. 6, 2003.

Gopinath, Ashwin, et al., Deterministic Aperiodic Arrays of Metal Nanoparticles for Surface-enhanced Raman Scattering (SERS), Publication Date: Mar. 2, 2009; vol. 17; On pp. 3741-3753, <http://www.bio-page.org/boriskina/Boriskina_OE2009.pdf>.

Guieu, Valérie, et al., "Multitip-localized enhanced Raman scattering from a nanostructured optical fiber array," The Journal of Physical Chemistry C 113.3 (2008): 874-881.

International Search Report, Mar. 30, 2011, PCT Application No. PCT/US2010/044039, Filed Jul. 30, 2010.

Krishnamoorthy, Sivashankar, et al., Combining Micelle Self-assembly with Nanostencil Lithography to Create Periodic/aperiodic Micro-/nanopatterns on Surfaces, Publication Date: Jul. 30, 2008; vol. 20: On pp. 3533-3538.

Lucotti et al., "Fiber-optic SERS sensor with optimized geometry," Elsevier, ScienceDirect, Sensors and Actuators B, vol. 121, 2007, 356-364.

PCT International Search Report, Jan. 20, 2011, Hewlett-Packard Development Company, L.P. (PCT/US2010/031790, Filed Apr. 20, 2010).

PCT International Search Report, Dec. 23, 2010, Hewlett-Packard development Company, L.P. (PCT/US2010/031809, Filed Apr. 20, 2010).

Ren, Hongliang, et al. "The prepartaion of optical fibre nanoprobe and its application in spectral detection," Optics & Laser Technology 39.5 (2007): 1025-1029.

Segawa, H., et al., "Top-gathering pillar array of hybrid organic-inorganic material by means of self-organization", Applied Physics A—Materials Science & Proceeding, Mar. 17, 2006, vol. 83, pp. 447-451.

White, Daniel J., et al., "Nanostructured optical fibre for surface-enhanced Raman scattering sensing." Proc SPIE. vol. 7102. 2008.

Xie et al., "Polymer optical fiber SERS sensor with gold nanorods," Elsevier, Optics Communications, vol. 282, 2009, pp. 439-442.

Zhang et al., "Single-Fiber Probe Based on Surface Enhanced Raman Scattering (SERS)," IEEE Sensors, 2005, pp. 1088-1091.

* cited by examiner

PROBE HAVING NANO-FINGERS

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that results when the material is illuminated by a form of electromagnetic radiation (for instance, visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman scattering.

Raman scattering optical spectroscopy employs an emission spectrum or spectral components thereof produced by inelastic scattering of photons by an internal structure of the material being illuminated. These spectral components contained in a response signal (for instance, a Raman signal) may facilitate determination of the material characteristics of an analyte species including identification of the analyte.

The Raman signal level or strength may be significantly enhanced by using a tip-enhanced Raman spectroscopy (TERS) technique. In recent years, TERS has emerged as a routine and powerful tool for investigating molecular structures and characterizing interfacial and thin-film systems, and even enables single-molecule detection.

BRIEF DESCRIPTION OF THE DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Disclosed herein are a probe and an apparatus for using in a sensing application. Also disclosed herein is a method for fabricating the probe. The probe includes a plurality of nano-fingers that are composed of a flexible material and are collapsed toward each other such that the tips of the nano-fingers are substantially in contact with each other. In other words, the tips of the nano-fingers are either in contact with each other or are separated by a very small distance on the order of less than about 1 nm. In addition, Raman-active material nano-particles are attached to respective tips of the nano-fingers. In one implementation, the probe is positioned in close relation to a sample to enable a TERS operation to be performed on the sample.

Through implementation of the probe, apparatus, and method of fabricating the probe disclosed herein, TERS operations (as well as atomic force microscopy (AFM) operations) may substantially be enhanced over TERS (and AFM) operations that use conventional probes. In one regard, the use of multiple nano-fingers having Raman-active material nano-particles attached to the tips of the multiple nano-fingers generally enhances the electromagnetic field generation and therefore the Raman scattering of light from a sample. In other words, the closely positioned nano-particles on the nano-fingers enables hot-spots to have a larger electric field strength as compared with Raman-active material nano-particles that have simply been placed on the component layer because, for instance, the use of the nano-fingers enables the formation of relatively small (less than about 10 nm wide) gaps between adjacent nano-particles.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared and ultraviolet portions of the electromagnetic spectrum.

Figure 1A:
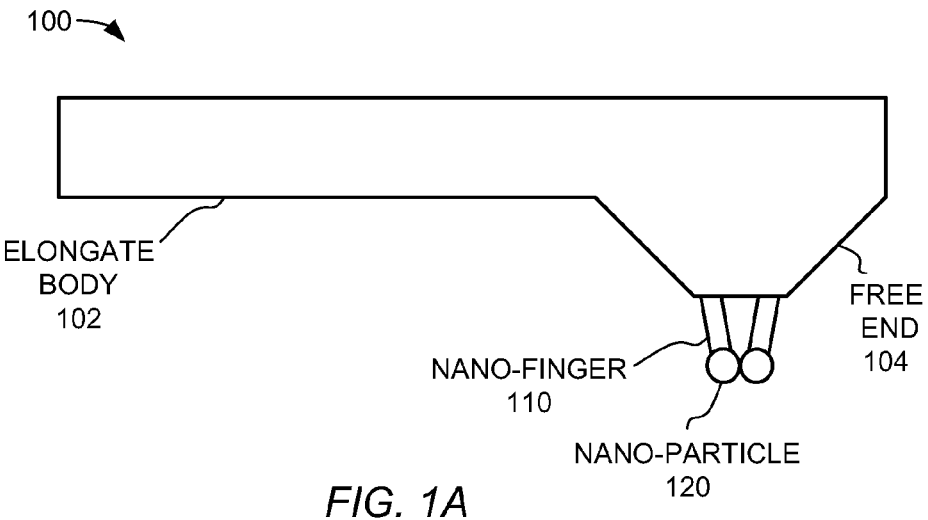
FIG. 1A shows a side view of a probe for use in a sensing application, according to an example of the present disclosure.

FIG. 1A shows a side view of a probe 100 for use in a sensing application, according to an example. It should be understood that the probe 100 depicted in FIG. 1A may include additional elements and that some of the elements described herein may be removed and/or modified without departing from a scope of the apparatus 100. It should also be understood that the elements depicted in FIG. 1A are not drawn to scale and thus, the elements may have different relative sizes with respect to each other than as shown therein.

According to an example, the sensing application for which the probe 100 is to be used includes tip enhanced Raman spectroscopy (TERS). More particularly, for instance, the probe 100 is to be moved spatially, for instance, in two or more dimensions, to enable TERS to be performed at multiple locations of a sample. According to an example, the probe 100 is to be used in atomic force microscopy (AFM), which shows the TERS effect.

As shown in FIG. 1, the probe 100 is composed of an elongate body 102 having a free end 104. The end opposite the free end 104 on the elongate body 102 is to be connected to a support (not shown). In this regard, the probe 100 is to be cantilevered from the support. The support may also be connected to an actuator (not shown), such as a piezoelectric actuator, micro-electro-mechanical system, etc., that is able to vary the spatial position of the probe 100.

The elongate body 102 may have any suitable cross-sectional shape, such as, circular, rectangular, triangular, etc., and has cross-sectional dimensions in the nanometer range. In one example, the elongate body 102 has sufficiently large dimensions, for instance, based upon the type of material from which the elongate body 102 is formed, to be relatively rigidly cantilevered from the support. Examples of suitable materials for the elongate body 102 include, silicon, silicon nitride, glass, plastic, polymer, $SiO_2$, $Al_2O_3$, gold, silver, copper, platinum, aluminum, etc., or a combination of these metals in the form of alloys, etc.

As also shown in FIG. 1, a plurality of nano-fingers 110 are attached to a bottom surface of the elongate body 102 at the free end 104. The nano-fingers 110 are formed of a relatively flexible material to enable the nano-fingers 110 to be laterally bendable, for instance, to enable tips of the nano-fingers 110 to move toward each other, as discussed in greater detail herein below. Examples of suitable materials for the nano-fingers 110 include polymer materials, such as, polydimethylsiloxane (PDMS) elastomer, polyimide, polyethylene, polypropelene, fluoropolymer, etc., or any combination thereof, metallic materials, such as, gold, silver, aluminum, etc., semiconductor materials, etc., and combinations thereof. In various examples, the nano-fingers 110 may be fabricated through a nanoimprinting or embossing process in which a template of relatively rigid pillars is employed in a multi-step imprinting process on a polymer matrix to form the nano-fingers 110. Various other processes, such as, etching, and various techniques used in the fabrication of micro-electromechanical systems (MEMS) and nano-electromechanical systems (NEMS) may also be used to fabricate the nano-fingers 110.

A nano-finger 110 may be defined as an elongated, nanoscale structure having a length (or height) that exceeds by more than several times a nanoscale cross sectional dimension (for instance, width) taken in a plane perpendicular to the length (for instance, length>3×width). In general, the length is much greater than the width or cross sectional dimension to facilitate bending of the nano-finger 110 laterally onto one or more neighboring nano-fingers 110. In some examples, the length exceeds the cross sectional dimension (or width) by more than a factor of about 5 or 10. For example, the width may be about 100 nanometers (nm) and the height may be about 500 nm. In another example, the width at the bases of the nano-fingers 110 may range between about 10 nm and about 1 micrometer (μm) and the length may range between about 50 nm and 2 μm. In other examples, the nano-fingers 110 are sized based upon the types of materials used to form the nano-fingers 404. Thus, for instance, the more rigid the material(s) used to form the nano-fingers 110, the less the width of the nano-fingers 110 may be to enable the nano-fingers 110 to be laterally collapsible. In further examples, the nano-fingers 110 may form ridges in which two of three dimensions (for instance, length and height) exceed by more than several times a nanoscale cross sectional dimension (for instance, width). The nano-fingers 110 may equivalently be referenced as nanopoles or nanopillars without departing from a scope of the probe 100.

According to an example, the nano-fingers 110 are arranged with respect to each other on the probe 100 such that the tips of the nano-fingers 110 are able to touch each other when the nano-fingers 110 are in a collapsed state. By way of particular example, the nano-fingers 110 are positioned between about 10 to 500 nm apart from each other.

The nano-fingers 110 have been depicted as having substantially cylindrical cross-sections. It should, however, be understood that the nano-fingers 110 may have other shaped cross-sections, such as, for instance, rectangular, square, triangular, etc. In addition, or alternatively, the nano-fingers 110 may be formed with one or more features, such as, notches, bulges, etc., to substantially cause the nano-fingers 110 to be inclined to collapse in particular directions. Thus, for instance, two or more adjacent nano-fingers 110 may include the one or more features to increase the likelihood that the nano-fingers 110 collapse toward each other. Various manners in which the nano-fingers 110 may be collapsed are described in greater detail herein below.

As also shown in FIG. 1A, nano-particles 120 are provided on the tips of the nano-fingers 110. The nano-particles 120 generally comprise Raman-active material nano-particles. The Raman-active material nano-particles 120 comprise a metal, such as, gold, silver, copper, platinum, aluminum, etc., or a combination of these metals in the form of alloys, or other suitable material that is able to support surface plasmons for field enhancement for Raman scattering. In addition, the Raman-active material nano-particles 120 may be multilayer structures, for example, 10 to 100 nm silver layer with 1 to 50 nm gold over-coating, or vice versa. By definition herein, a Raman-active material is a material that facilitates Raman scattering from a sample positioned near the Raman-active material during Raman spectroscopy.

Any reasonably suitable number of nano-fingers 110 may be attached to the elongate body 102 and arranged in any suitable spatial configuration. Examples of various suitable spatial configurations are depicted in FIGS. 1B-1F. More particularly, FIGS. 1B-1F respectively depict bottom views of the probe 100 according to multiple examples. It should be understood that the arrangements of the nano-fingers 110 as depicted in FIGS. 1B-1F are for illustrative purposes and that the nano-fingers 110 depicted in FIGS. 1B-1F may be configured in different spatial arrangements. For instance, the clusters of nano-fingers 110 and nano-particles 120 may be rotated with respect to their depicted configurations.

Figure 1B:
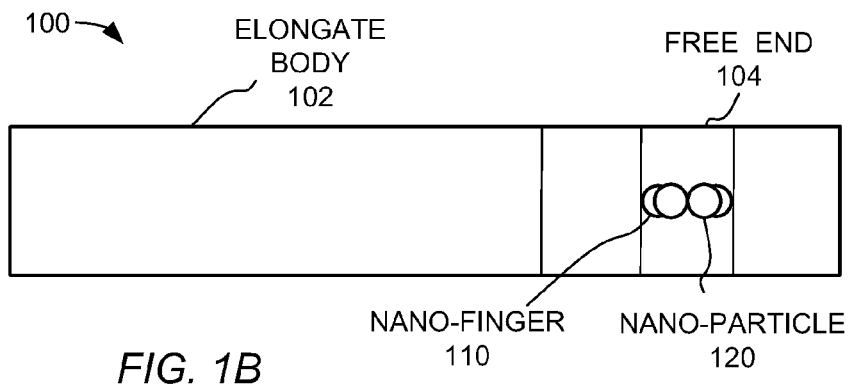
FIGS. 1B-1F, respectively, show bottom views of the probe depicted in FIG. 1A, according to examples of the present disclosure.
Figure 1C:
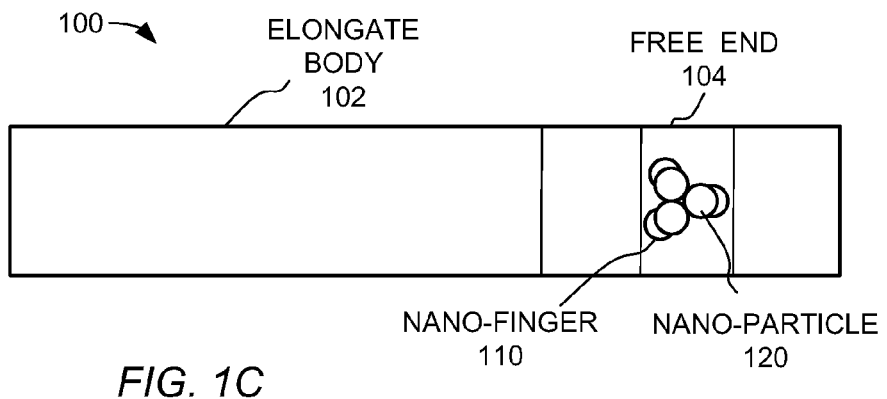
Figure 1D:
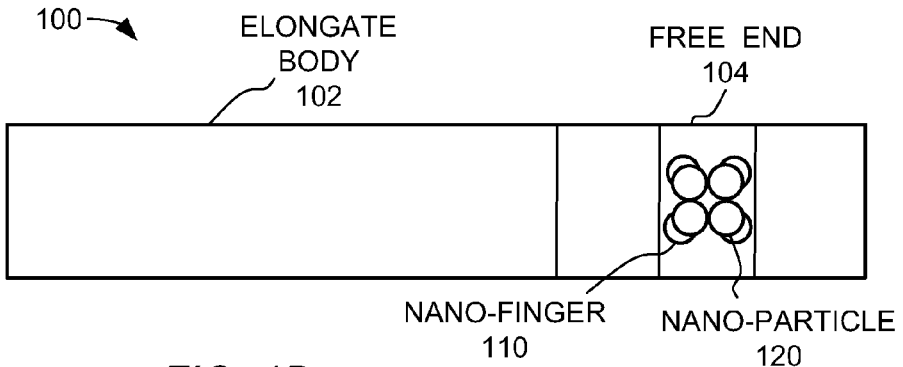
Figure 1E:
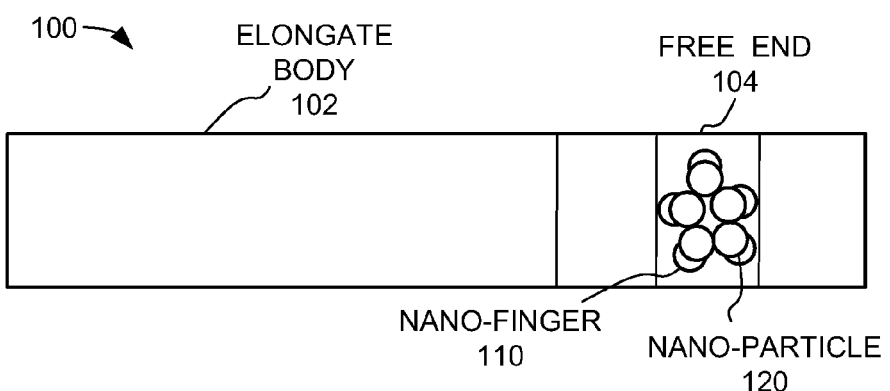
Figure 1F:
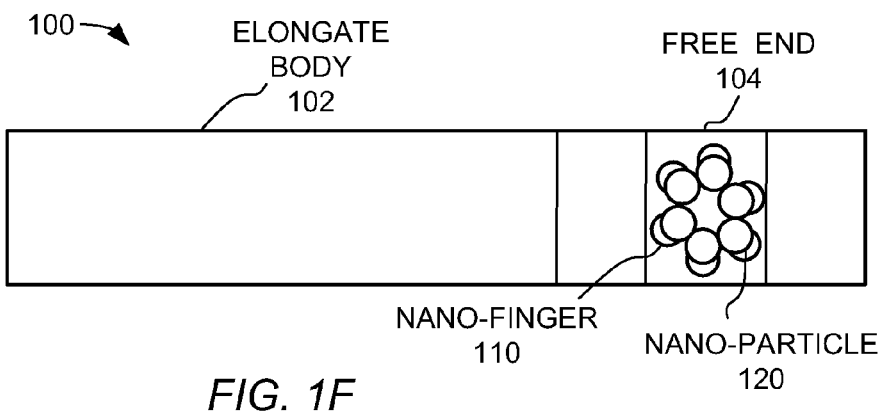

In FIG. 1B, two nano-fingers 110 are depicted as being in contact with each other in a dimer configuration. In FIG. 1C, three nano-fingers 110 are depicted as being in contact with each other in a trimer configuration. In FIG. 1D, four nano-fingers 110 are depicted as being in a tetramer configuration. In FIG. 1E, five nano-fingers 110 are depicted as being in a pentamer configuration. In FIG. 1F, six nano-fingers 110 are depicted as being in a hexamer configuration.

The probe 100 has thus been depicted in FIGS. 1B-1F as containing particular numbers of nano-fingers 110 and thus, particular numbers of nano-particles 120. It should, however, be understood that the probe 100 may include any number of nano-fingers 110 and nano-particles 120 arranged in any suitable spatial configuration in which a plurality of the nano-particles 120 are in contact with each other without departing from a scope of the probe 100.

According to an example, the Raman-active material nano-particles 120 in a cluster of nano-fingers 110 are attached to each other with a gap between at least two of the Raman-active material nano-particles 120 being less than about 10 nm in width. More particularly, the Raman-active material nano-particles 120 in a cluster of nano-fingers 110 are attached to each other with a gap being less than between about 0.5 nm and 5 nm. Generally speaking, the relatively small gaps between the Raman-active material nano-particles 120 in each of the clusters of nano-fingers 110 may be achieved through implementation of the fabrication methods disclosed herein.

Figure 2:
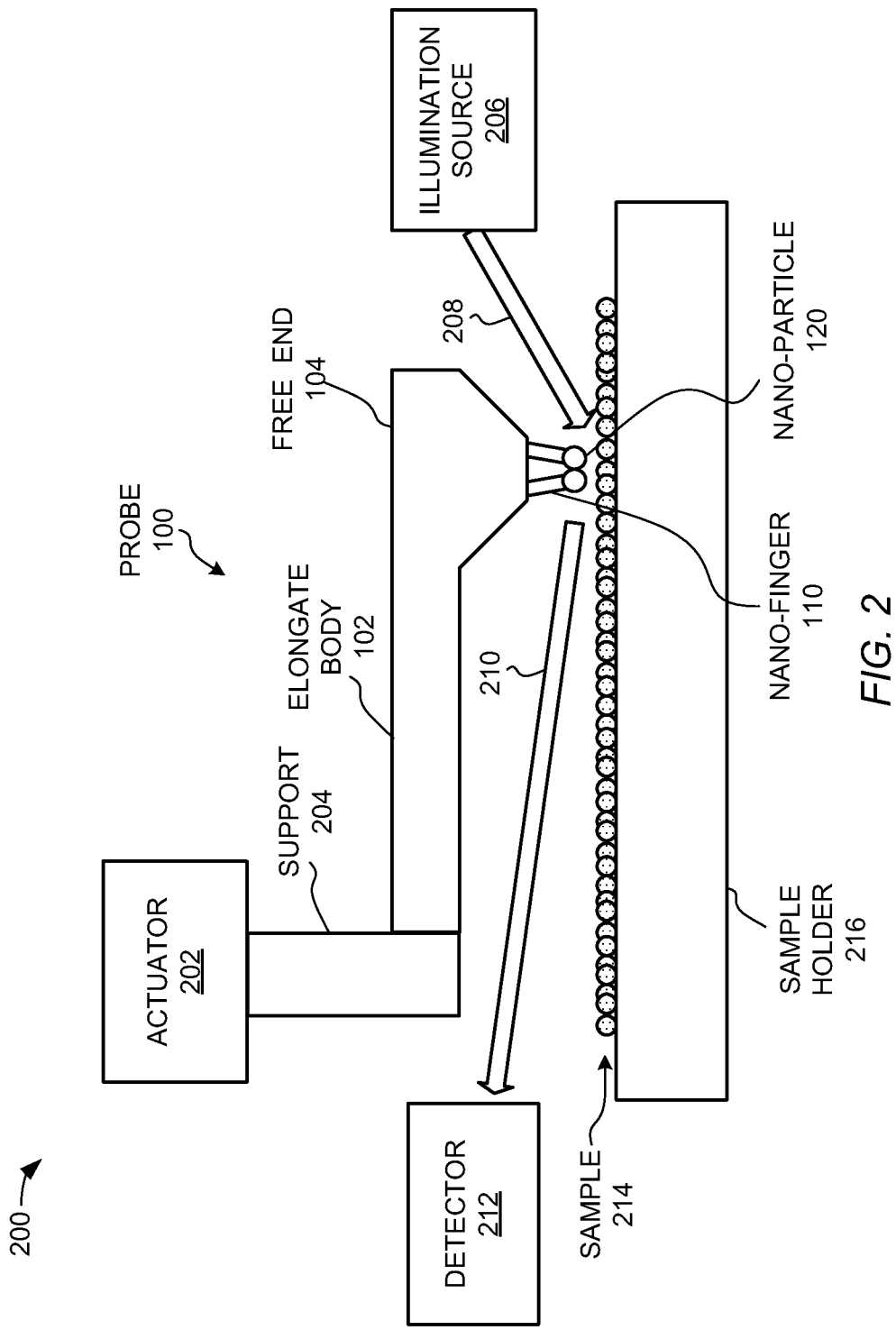
FIG. 2 shows a block diagram of an apparatus for use in a sensing application, according to an example of the present disclosure.

With reference now to FIG. 2 there is shown a block diagram of an apparatus 200 for use in a sensing application, according to an example. It should be understood that the apparatus 200 may include additional elements and that some of the elements described herein may be removed and/or modified without departing from the scope of the apparatus 200. It should also be understood that the elements depicted in the apparatus 200 are not drawn to scale and thus, the elements may have different relative sizes with respect to each other than as shown therein.

As shown in FIG. 2, the apparatus 200 includes the probe 100 depicted in FIGS. 1A-1F, an actuator 202, a support 204, an illumination source 206, and a detector 212. A sample 214 to be tested is also depicted as being positioned on a sample holder 216. The probe 100 is depicted as being cantilevered from the support 204 at an end opposite the free end at which the nano-fingers 110 are attached or otherwise positioned on the probe 100. The support 204 is also depicted as being connected to the actuator 202. In this regard, the actuator 202 may vary the spatial position, for instance, in at least one dimension, of the nano-fingers 110 to thereby vary the location on the sample 214 at which TERS operations are performed.

The illumination source 206 is depicted as emitting electromagnetic radiation, as represented by the arrow 208, which may comprise, for instance, light. By way of example, the illumination source 206 may comprise a laser that illuminates the sample 214 and the Raman-active material nano-particles 120. Illumination of the Raman-active material nano-particles 120 causes hot spots of relatively large electric field strength to occur. The hot spots are increased at the locations where the Raman-active material nano-particles 120 contact each other. The electric fields generated at the contact locations between the Raman-active material nano-particles 120 generally enhance the rate at which Raman light is scattered by the sample 214 positioned at or near the contact locations. The Raman scattered light, which is represented by the arrow 210, is shifted in frequency by an amount that is characteristic of particular vibrational modes of the sample 214. The detector 212 is to collect the Raman scattered light 210 and spectral analysis may be performed on the Raman scattered light 210.

The Raman-active material nano-particles 120 located near or adjacent to the sample 214 location may enhance the production of Raman scattered light 210 from that location of the sample 214 by concentrating or otherwise enhancing an electromagnetic field in a vicinity of that sample 214 location. In this regard, the likelihood that the sample 214 will produce sufficiently strong Raman scattered light 210 to be detected by the detector 212 will thus also be increased.

Although the Raman scattered light 210 has been depicted as being directed toward the detector 214, the Raman scattered light 210 is emitted in multiple directions. In this regard, some of the Raman scattered light 210 may be directed into the sample holder 216, which may comprise an optical waveguide. More particularly, for instance, Raman scattered light 210 may be generated in the sample holder 216 as a result of the sample 214 coupling to the evanescent field of a waveguide mode. In these instances, the detector 212 may be positioned to detect the waves generated in the sample holder 216 from the Raman scattered light 210. In any regard, the detector 212 may include a filter to filter out light originating from the illumination source 206, for instance, through use of a grating-based monochromer or interference filters.

The detector 212 is generally to convert the Raman scattered light 210 emitted from the sample 214 into electrical signals. In some examples, the detector 212 is to output the electrical signals to other components (not shown) that are to process the electrical signals, such as, a computing device. In other examples, the detector 212 is equipped with in the processing capabilities.

According to an example, the apparatus 200 comprises a system that is integrated on a single chip. For example, the output of the sample holder 216 may be connected to an arrayed waveguide grating (AWG filter). The sample holder 216 may also be directly coupled to optical fibers in the apparatus 200 through which the illumination light 208 may be supplied and through which the Raman scattered light 210 may be outputted. In this example, the apparatus 200 provides a relatively more compact solution than coupling free-space signals to fibers. Additionally, the apparatus 200 may be implemented efficiently for a relatively large sensing area for which the free-space signals are substantially more complex and/or expensive to implement. The sample holder 216 may also be directly coupled to optical fibers in particular instances to form compact field sensors. In this instance, the illumination source 206, for instance an excitation laser, and the detector 212, for instance, spectral analysis equipment, may be housed in a remote location.

Figure 3:
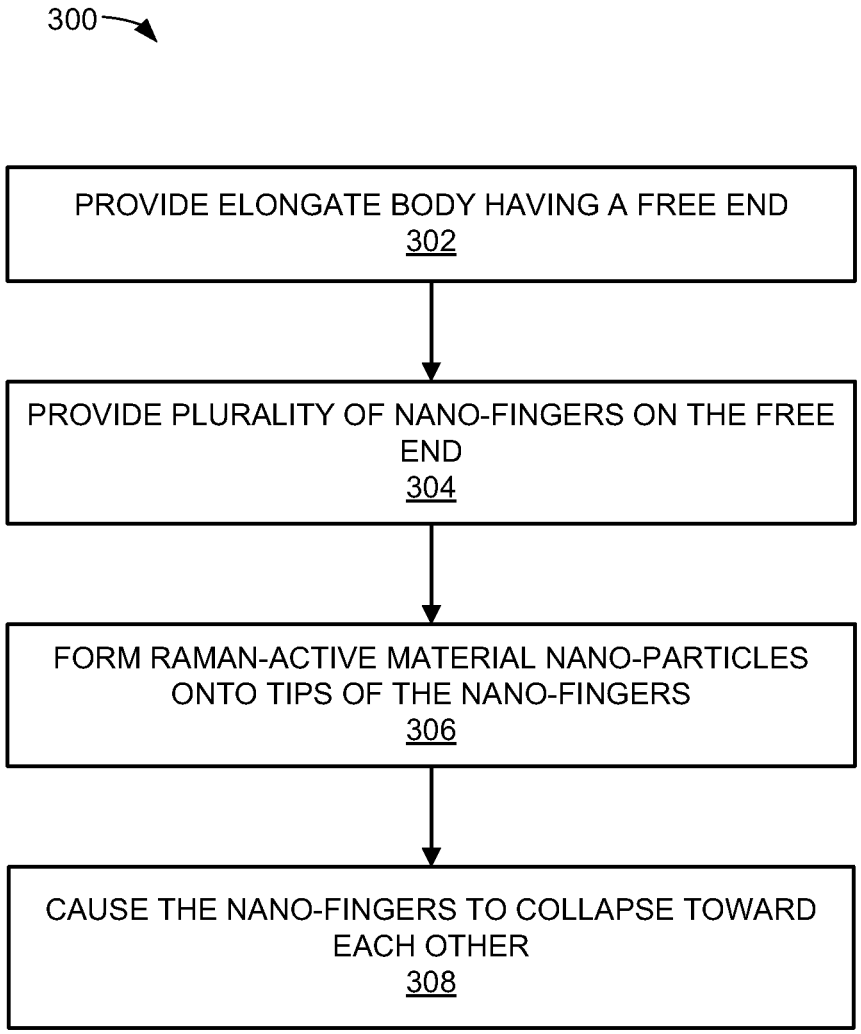
FIG. 3 shows a flow diagram of a method for fabricating a probe for use in a sensing application, according to an example of the present disclosure.

Turning now to FIG. 3, there is shown a flow diagram of a method 300 for fabricating a probe for use in a sensing application, according to an example. It should be understood that the method 300 may include additional processes and that some of the processes described herein may be removed and/or modified without departing from a scope of the method 300.

At block 302, an elongate body 102 having a free and 104 is provided. As discussed above, the elongate body 102 may comprise cross-sectional dimensions in the nanometer range and may be composed of various types of materials.

At block 304, a plurality of nano-fingers 110 are provided on the free end 104 of the elongate body 102. According to an example, the nano-fingers 110 are formed in a predetermined arrangement on a surface of the elongate body 102 to substantially cause the nano-fingers 110 to be collapsible onto each other. Various examples of suitable arrangements of the nano-fingers 110 have been depicted in FIGS. 1B-1F.

According to an example, a nanoimprinting technique or a roll-to-roll process may be implemented to form the nano-fingers 110 on the surface of the elongate body 102. In this example, a template may be formed through photolithography or other advanced lithography with the desired patterning to arrange the nano-fingers 110 in the predetermined arrangement. More particularly, for instance, the desired patterns may be designed on a mold, by E-beam lithography, photolithography, laser interference lithography, Focused Ion Beam (FIB), self-assembly of spheres, etc. In addition, the pattern may be transferred onto, for instance, silicon, glass, or polymer substrate (PDMS, polyimide, polycarbonate, etc.). In other examples, the nano-fingers 110 may be formed in the predetermined arrangement through implementation of any suitable fabrication process.

The nano-fingers 110 may be provided on the surface of the elongate body 102 through any suitable attachment mechanism. For instance, the nano-fingers 110 may be grown directly on the surface of the elongate body 102 through use of various suitable nano-structure growing techniques. As another example, the nano-fingers 110 may be integrally formed with the elongate body 102. In this example, for instance, a portion of the material from which the elongate body 102 is fabricated may be etched or otherwise processed to form the nano-fingers 110. In a further example, a separate layer of material may be adhered to the elongate body 102 surface and the separate layer of material may be etched or otherwise processed to form the nano-fingers 110.

At block 306, respective Raman-active material nano-particles 120 are formed on the tips of the nano-fingers 110. In one example, the Raman-active material nano-particles 120 may be formed of a collection of atoms or atom clusters. Moreover, the Raman-active material nano-particles 120 may have various other shapes than those depicted in FIGS. 1A-1F and 2. For instance, the Raman-active material nano-particles 120 may extend beyond an outer perimeter of the nano-fingers 110, extend along at least a portion of the nano-fingers 110, etc.

The atoms or atom clusters of the Raman-active material nano-particles 120 may be deposited onto the tips of the nano-fingers 110 through, for instance, physical vapor deposition (PVD), chemical vapor deposition (CVD), sputtering, etc., of metallic material, or self-assembly of pre-synthesized nano-particles. By way of example, the angle at which the atoms or atom clusters are deposited onto the tips of the nano-fingers 110 may be controlled to thereby substantially control the deposition of the atoms or atom clusters.

At block 308, the tips of the nano-fingers 110 are caused to collapse toward each other to thereby cause the Raman-active material nano-particles 120 on the tips of adjacent ones of the nano-fingers 110 to contact each other. According to an example, the nano-fingers 110 may initially be in a first position, in which their tips are in a substantially spaced arrangement with respect to each other. The gaps between the tips of the nano-fingers 110 may be of sufficiently large size to enable a liquid to be supplied in the gaps. In addition, the gaps may be of sufficiently small size to enable the tips of the nano-fingers 110 to move toward each other as the liquid evaporates, through, for instance, capillary forces applied on the tips as the liquid dries. Other non-limiting examples, such as e-beam, ion-beam, magnetic, mechanical force, thermal effect, or electric charge effect, may also or instead be utilized to cause the tips of the nano-fingers 110 to move toward each other. In any regard, the Raman-active material nano-particles 120 may contact each other and remain in contact with each other through, for instance, van der Waals interactions between those contacting nano-particles 120.

According to another example, blocks 306 and 308 may be reversed with each other. In other words, the Raman-active material nano-particles 120 may be formed on the tips of the nano-fingers 110 following the collapsing of the nano-fingers toward each other.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. A probe for use in a sensing application, said probe comprising:
   an elongate body having a first end and a free end, wherein the first end is to be attached to a support, and wherein the free end includes a section that extends beneath the elongate body, said section having a surface that is substantially parallel to the elongate body; and
   a plurality of nano-fingers having respective bases and tips, wherein each of the plurality of nano-fingers is attached to the surface of the section in the free end and is composed of a flexible material, and wherein the plurality of nano-fingers are collapsed toward each other such that the tips of the plurality of nano-fingers are substantially in contact with each other.

2. The probe according to claim 1, further comprising:
   Raman-active material nano-particles attached to respective tips of the plurality of nano-fingers, wherein the Raman-active material nano-particles are substantially in contact with each other.

3. The probe according to claim 1, wherein the elongate body comprises part of an atomic force microscopy probe for use in tip-enhanced Raman spectroscopy.

4. The probe according to claim 1, wherein the plurality of nano-fingers are arranged in one of a dimer, trimer, tetrameter, pentamer, and hexamer configuration on the free end of the elongate body.

5. The probe according to claim 1, wherein the bases of the plurality of nano-fingers are spaced at less than about 10 nm from each other.

6. The probe according to claim 1, wherein the elongate body is composed of a material selected from the group consisting of silicon, silicon nitride, glass, plastic, polymer, $SiO_2$, $Al_2O_3$, metal, and combinations thereof.

7. The probe according to claim 1, wherein the plurality of nano-fingers is composed of material selected from the group consisting of polydimethylsiloxane (PDMS) elastomer, polyacrylate, polyimide, polyethylene, polypropelene, fluoropolymer, gold, silver, aluminum, semiconductor materials, and combinations thereof.

8. An apparatus for use in a sensing application, said apparatus comprising:
   an actuator having a support;
   a probe having a first end and a free end, wherein the probe is cantilevered from the support at the first end and wherein the free end includes a section that extends beneath the elongate body, said section having a surface that is substantially parallel to the elongate body, said probe having,
      a plurality of nano-fingers having respective bases and tips, wherein each of the plurality of nano-fingers is attached to the surface of the section in the free end and is composed of a flexible material, and wherein the plurality of nano-fingers are collapsed toward each other such that the tips of the plurality of nano-fingers are substantially in contact with each other; and
      Raman-active material nano-particles attached to respective tips of the plurality of nano-fingers, wherein the Raman-active material nano-particles are substantially in contact with each other;
   an illumination source to illuminate the Raman-active material nano-particles; and
   a detector positioned to detect Raman scattered light emitted from a sample positioned in close proximity to the Raman-active material nano-particles.

9. The apparatus according to claim 8, wherein the plurality of nano-fingers are arranged in one of a dimer, trimer, tetrameter, pentamer, and hexamer configuration on the free end of the elongate body.

10. The apparatus according to claim 8, wherein the plurality of nano-fingers is composed of material selected from the group consisting of polydimethylsiloxane (PDMS) elastomer, polyacrylate, polyimide, polyethylene, polypropelene, fluoropolymer, gold, silver, aluminum, semiconductor materials, and combinations thereof.

11. A method of fabricating a probe for use in a sensing application, said method comprising:
   providing an elongate body having a free end, wherein the free end includes a section that extends beneath the elongate body, said section having a surface that is substantially parallel to the elongate body;

providing a plurality of nano-fingers on the surface of the section in the free end of the elongate body, wherein each of the plurality of nano-fingers has a base and a tip, and wherein the plurality of nano-fingers are composed of a flexible material;

forming Raman-active material nano-particles onto the tips of the plurality of nano-fingers; and causing the plurality of nano-fingers to collapse toward each other to cause respective tips of the plurality of nano-fingers to be substantially in contact with each other.

12. The method according to claim 11, wherein providing the plurality of nano-fingers further comprises forming the plurality of nano-fingers on a surface of the elongate body.

13. The method according to claim 12, wherein forming the plurality of nano-fingers further comprises forming the plurality of nano-fingers through implementation of at least one of a nanoimprinting technique and an embossing process.

14. The method according to claim 11, wherein causing the plurality of nano-fingers to collapse toward each other further comprises introducing a liquid between the plurality of nano-fingers and evaporating the liquid, wherein the capillary forces cause the plurality of nano-fingers to collapse toward each other as the liquid evaporates.

15. The method according to claim 11, further comprising:
forming the Raman-active material nano-particles onto the tips of the plurality of nano-fingers prior to causing the nano-fingers to collapse toward each other.

* * * * *

UNITED STATES PATENT AND TRADEMARK OFFICE
CERTIFICATE OF CORRECTION

PATENT NO.        : 8,605,281 B2
APPLICATION NO.   : 13/272987
DATED             : December 10, 2013
INVENTOR(S)       : Zhiyong Li et al.

Page 1 of 1

It is certified that error appears in the above-identified patent and that said Letters Patent is hereby corrected as shown below:

In the Claims

Column 8, lines 10-11, in Claim 4, delete "tetrameter," and insert -- tetramer, --, therefor.

Column 8, line 23, in Claim 7, delete "polypropelene," and insert -- polypropylene, --, therefor.

Column 8, lines 53-54, in Claim 9, delete "tetrameter," and insert -- tetramer, --, therefor.

Signed and Sealed this
Thirteenth Day of May, 2014

Michelle K. Lee
*Deputy Director of the United States Patent and Trademark Office*